United States Patent [19]

Weeks

[11] Plant 4,007

[45] Jan. 4, 1977

[54] ROSE PLANT

[76] Inventor: O. L. Weeks, 926 W. Philadelphia, Ontario, Calif. 91761

[21] Appl. No.: 671,273

[22] Filed: Mar. 29, 1976

[51] Int. Cl.[2] ..... A01H 5/00

[52] U.S. Cl. ..... Plt./12

[58] Field of Search ..... Plt./12, 22

*Primary Examiner*—Robert E. Bagwill

*Attorney, Agent, or Firm*—Robb & Robb

CLAIM

A new and distinct variety of rose plant of the hybrid tea class, substantially as herein shown and described, characterized particularly as to novelty by the unique combination of strong, extremely thorny stems carrying a great many thorns, flowers or large, many petaled and excellent substance, with vivid red and yellow bi-coloring.

1 Drawing Figure

The present invention relates to a new and distinct variety of rose plant of the hybrid tea class, which was originated by me by crossing the rose variety known as "Sunrise-Sunset" (U.S. Plant Pat. No. 3,244) which I have chosen to identify in my breeding records as No. 6651-12 with a rose variety known as "Peace" (U.S. Plant Pat. No. 591), the seedling No. 6651-12 being the seed parent and the pollen parent being the variety "Peace". As the result of this breeding, I have produced a new and improved rose variety distinguished from its parents, as well as from all other rose varieties of which I am aware, evidenced by the following unique combination of principal characteristics which are outstanding in the new variety:

1. The stems are strong and extremely thorny;
2. Flowers are large and many petaled, and have excellent substance; and
3. A distinctive flower of vivid red and yellow bi-coloring distinguishing this new seedling particularly.

Comparing my new variety with the seed parent, it is noted that the seed parent variety lacks the prolific blooming habit of my new variety; and the petal substance of the parent plant is not as good as in the seedling, whereas the flowers of the new variety are a true bi-color with cherry red inside petals and straw yellow at the base.

In comparison with the pollen parent ("Peace"), the new variety is a substantially taller growing plant than the pollen parent, and the flowers are not as large although many petaled, having fewer petals than ("Peace") being more of an overall light yellow with pink edgings whereas the instant seedling is a definite combination of red on the inside petals and yellow on the outside petals, making it a true bi-color and not a blend of shades.

Asexual reproduction of my new variety by budding, performed by me at Chino, Cal., demonstrates that the aforementioned characteristics and depth and distinction come true to form, are established, and are transmitted through succeeding propagations.

The accompanying drawing shows typical specimens of the vegetative growth and flowers of my new variety in different stages of development, and as depicted in color as nearly true as is reasonably possible to make the same in a color illustration of this character.

There is set forth in the following, a detailed description of my new variety, the color terminology being in accordance with Munsell's Color Cascade, published by Munsell Color Company, Inc., of Baltimore, Md., except where general color terms of ordinary dictionary significance are obvious:

Type: Hardy
Class: Hybrid Tea
Breeding: Seedling.
- *Seed Parent.*—"Sunrise-Sunset" (U.S. Plant Pat. No. 3,244)
- *Pollen Parent.*—"Peace" (Plant Patent 591)
- *Propagation.*—Holds its distinguishing characteristics through succeeding propagations by budding

FLOWERS

Locality where grown and observed: Chino, Calif.
Flowers born: From singly, 2 or 3 to a stem; in regular clusters on normally strong, medium, long stems.
Quantity of bloom: Free and abundant, both outdoors and in the greenhouse.
Continuity: From intermittent to continuous during the season.
Fragrance: Moderate.
Bud: Peduncle—Short to medium length; medium caliper; erect and stiff; somewhat rough; with reddish brown hairs and small prickles.
- *Color.*—Reddish green.
- *Before calyx breaks.*—Size—Medium Form—Medium to small length; globular almost with a conspicuous neck; slightly foliaceous appendages on the surface of the bud; with slender bristle-like foliaceous parts extending beyond the tip of the bud equal to about ½ to ¾ or more of its length.
- *As calyx breaks.*—Color—Dark reddish purple.
- *As petal first opens.*—Size—Small to medium. Form—Long slightly pointed and mostly globular. Color—Outside: Cardinal Red 39-14 intermixed with splotches of buttery yellow 27-8. Inside: Cherry Red 38-13 with a hint of yellow at the base 27-5 Opening: Opens up well.

Bloom:
- *Size.*—(When fully open) from 3¼ inches to 4¼ inches.
- *Petalage.*—Double (more petals, but the stamens are not hidden); from 42 to 52 petals; arranged regularly.
- *Form.*—Cupped, high centered, somewhat ovid at first; petals being at first tightly cupped, rolled slightly outward but later becoming loosely cupped and rolled outward at maturity Petals:

*Texture.*—Moderately thick; somewhat velvety; soft

*Appearance.*—Inside: Satiny and velvety. Outside: Satiny.

*Shape.*—Outside: Obovate; slightly scalloped with apex flat, with 2 to 3 notches. Intermediate: Obovate; scalloped with apex somewhat flat with 2 to 3 notches. Inside: Obovate; with apex somewhat pointed, with 2 to 3 notches.

This description of a newly opened flower was made from a rose grown outdoors in the month of September at Ontario, Calif.

*Color.*—Outer Petal: Outside surface: Bright Yellow 25-5 bottom, fading quickly to a 29-2 blending into Fleshtone 33-2 half way up changing to a Pinkish Red 39-6. Inside surface: Buttery Yellow 27-5, abruptly changing to Cherry Red 40-10, ¼ inch from bottom with occasional white streaks running the length of the petal. Intermediate Petal: Outside surface: Medium Yellow 27-3 at the base blending slowly upward into Fleshtone 31-2 with border of petal being Salmon Pink 38-6. Inside surface: Medium Yellow 27-5 blending sharply ¼ inch from bottom into Orange Red 38-9. Inner Petal: Outside surface: Medium Yellow 27-5 blending upward to a Lighter Yellow 27-3, gradually changing to a Pink-Red 39-6 near the top. Inside surface: Medium Yellow 27-5 changing sharply ¼ inch from bottom into Orange-Red 38-9.

The following description is of a rose that was open for three days outdoors during the month of September at Ontario, Calif.

*Color.*—Outer Petal: Outside surface: Lemon Yellow 28-5 blending slowly into Pale Pink 42-5 with Yellow streaks 27-2 into a medium Salmon Pink 41-13 around the edges. Inside surface: Bright Lemon Yellow 26-6 at the base, abruptly changing to a Cherry Red 40-10 with an occasional white steak. Inner Petal: Outside surface: Bright Greenish Yellow 26-4 at base spreading upward to a Pale Yellow 29-3 blending at the top to a light to medium Pink 39-5. Inside surface: Bright Yellow 27-4 at the base blending to Light Yellow 27-3 and sharply changing to a Vermillion Red 40-7.

General color effect: Newly opened flower: Orange Red 38-9 with hint of Yellow 27-5 towards the inside. Three days open: Vermillion Red 40-7 at the top changing to a Lemon Yellow 27-4 near the bottom.

Behavior: Drop off cleanly.

Flower longevity: On bush in garden: 3 to 4 days in the month of September. Cut: Cut roses grown outdoors and kept at living-room temperatures—3 to 4 days in September.

REPRODUCTIVE ORGANS

Stamens: Medium number; arranged regularly about pistils; tucked in calyx.

Filaments: Short to mediumlength; many with anthers

*Color.*—Lemon Yellow.

Anthers: Medium size; open at various times

*Color.*—Yellow Orange.

Pollen: Sparse to moderate.

*Color.*—Gold Yellow.

Pistils: Medium number.

Styles: Even; short to medium length; medium caliper; bunched; columnar.

Stigma:

*Color.*—Pale Yellow.

Ovaries: All enclosed in calyx.

Hips: None observed.

Sepals: Permanent; moderate to short length; spear-shaped, recurved slightly.

*Color.*—Green with Reddish Purple shading.

Seeds: None observed.

PLANT

Foliage:

*Leaves.*—Compound of 3 to 5 leaflets; moderately sparse; moderately small to medium size; moderately thin and light weight in texture; somewhat wrinkled.

*Leaflets.*—Shape: Ovate; with apex obtuse; base round, coarsely serrate.

*Color.*—Mature: Upper surface—Moderately dark green; Under surface—Light yellowish green. Young: Upper surface—Light yellowish green; Under surface—Very light green.

*Rachis.*—(the supporting stem of the compound leaf) Medium to heavy weight; Upper side: smooth; slightly grooved; slightly prickly; Under side: moderately smooth; somewhat prickly.

*Stipules.*—Short to medium length; moderately narrow width; with moderately short points turning out at an angle of 45°.

*Disease Resistance.*—Normal. Good resistance to powdery mildew and rust as compared with other rose varieties grown under the same conditions in the same areas, and no evidence of black spot.

Growth:

*Habit.*—Bush; much branched.

*Growth.*—Vigorous.

*Canes.*—Medium to heavy caliper.

*Main Stems.*—Color: dull green.

*Large Prickles.*—Many; medium to long; hooked slightly downward; with long, narrow to broad base. Color: Muddy brown.

*Small Prickles.*—Many. Color: Brown.

*Hairs.*—None.

*Branches.*—Color: Dull, yellowish green

*Large Prickles.*—Several; medium to long; hooked downward with long narrow to broad base. Color: Muddy brown.

*Small Prickles.*—Many. Color: Reddish.

*Hairs.*—None.

*New Shoots.*—Color: Bright green at bottom changing to reddish maroon at top.

*Large Prickles.*—Many; medium; mostly hooked downward; with long narrow base. Color: Maroon.

*Small Prickles.*—Several. Color: Reddish maroon.

I claim:

1. A new and distinct variety of rose plant of the hybrid tea class, substantially as herein shown and described, characterized particularly as to novelty by the unique combination of strong, extremely thorny stems carrying a great many thorns, flowers or large, many petaled and excellent substance, with vivid red and yellow bi-coloring.

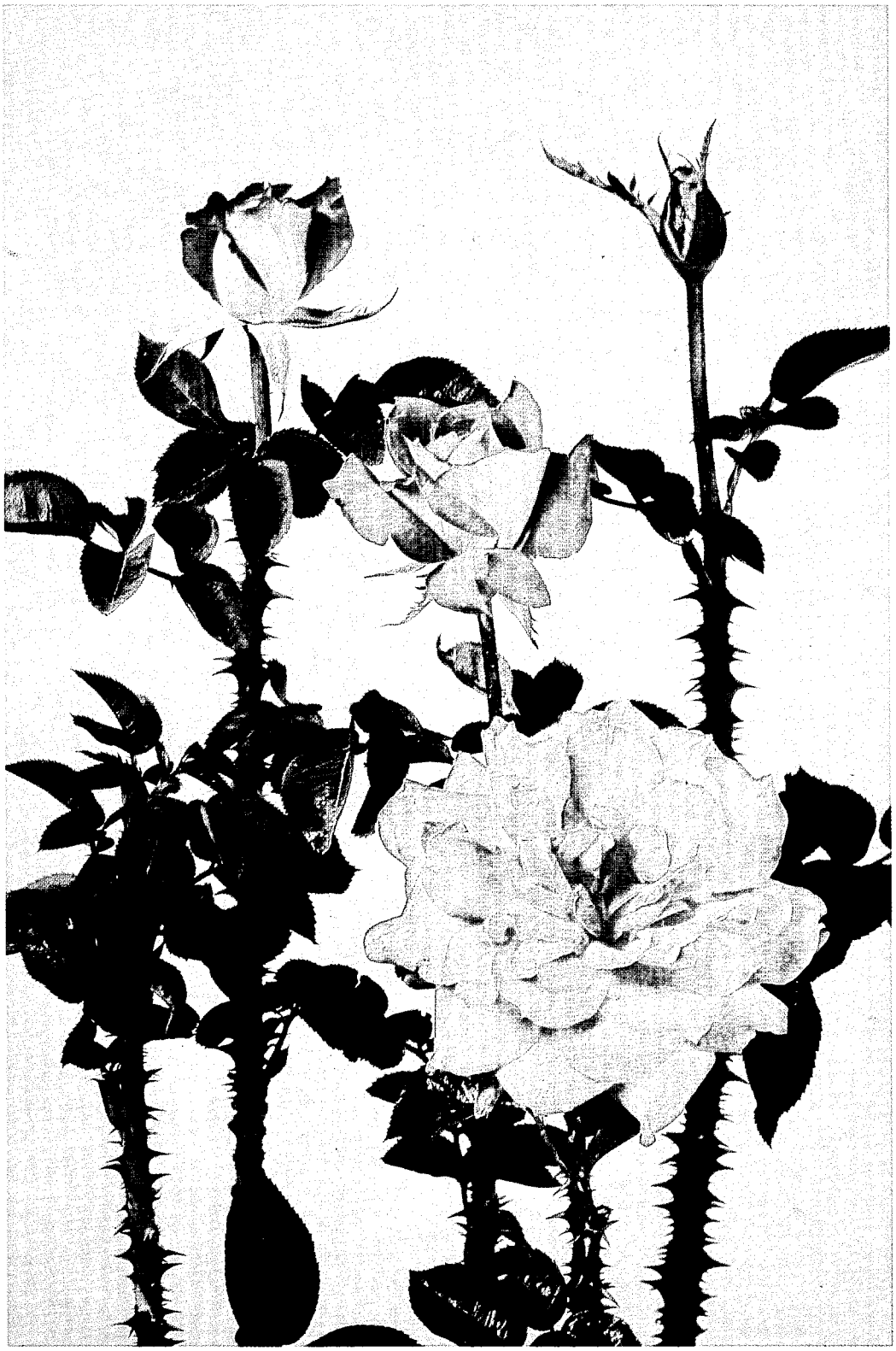

* * * * *